United States Patent [19]
Bruns et al.

[11] 4,033,993

[45] July 5, 1977

[54] CYCLOALKYL CARBONATES

[75] Inventors: Klaus Bruns, Krefeld-Traar; Peter Meins, Mettmann, both of Germany

[73] Assignee: Henkel & Cie G.m.b.H., Dusseldorf-Holthausen, Germany

[22] Filed: Apr. 14, 1976

[21] Appl. No.: 676,932

[30] Foreign Application Priority Data

Apr. 25, 1975 Germany .......................... 2518392

[52] U.S. Cl. ................................ 260/463; 252/522
[51] Int. Cl.² .................... C07C 69/96; A61K 7/46
[58] Field of Search .................................... 260/463

[56] References Cited

UNITED STATES PATENTS

| | | | |
|---|---|---|---|
| 2,885,278 | 5/1959 | Brack | 260/463 |
| 3,080,417 | 3/1963 | Rosen | 260/463 |
| 3,275,661 | 9/1966 | Widmer et al. | 260/463 |

FOREIGN PATENTS OR APPLICATIONS

| | | | |
|---|---|---|---|
| 2,234,797 | 1/1973 | Germany | 260/463 |

*Primary Examiner*—Delbert R. Phillips
*Attorney, Agent, or Firm*—Hammond & Littell

[57] ABSTRACT

Carbonic acid esters of the formula

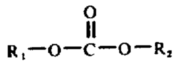

wherein $R_1$ is a member having from 8 to 12 carbon atoms selected from the group consisting of alkylcyclohexyl, alkenylcyclohexyl, alkynylcyclohexyl and cycloalkyl, and $R_2$ is a member selected from the group consisting of alkyl having from 1 to 5 carbon atoms, alkenyl having from 2 to 5 carbon atoms and alkynyl having from 2 to 5 carbon atoms, which compounds have pleasing and persistent scents, as well as processes for producing them and perfume compositions containing them.

5 Claims, No Drawings

CYCLOALKYL CARBONATES

OBJECTS OF THE INVENTION

An object of the present invention is the development of new ester compounds having very natural, pleasing and persistent scents, useful as perfumes.

Another object of the present invention is the development of a carbonic acid ester of the formula $$R_1-O-\overset{O}{\overset{\|}{C}}-O-R_2$$

wherein $R_1$ is a member having from 8 to 12 carbon atoms selected from the group consisting of alkylcyclohexyl, alkenylcyclohexyl, alkynylcyclohexyl and cycloalkyl, and $R_2$ is a member selected from the group consisting of alkyl having from 1 to 5 carbon atoms, alkenyl having from 2 to 5 carbon atoms and alkynyl having from 2 to 5 carbon atoms.

A further object of the present invention is the development of a process for the production of the above carbonic acid esters consisting essentially of reacting a cycloaliphatic alcohol of the formula $$R_1-OH$$

wherein $R_1$ is a member having from 8 to 12 carbon atoms selected from the group consisting of alkylcyclohexyl, alkenylcyclohexyl, alkynylcyclohexyl and cycloalkyl with a chloroformic acid ester of the formula $$Cl-\overset{O}{\overset{\|}{C}}-O-R_2$$

wherein $R_2$ is a member selected from the group consisting of alkyl having from 1 to 5 carbon atoms, alkenyl having from 2 to 5 carbon atoms and alkynyl having from 2 to 5 carbon atoms in an anhydrous, inert organic solvent in the presence of an HCl acceptor at a temperature of from 0° to 5° C, and recovering said carbonic acid ester.

A yet further object of the present invention is the production of a perfumery composition consisting essentially of from 1 to 50% by weight of the above carbonic acid esters and the remainder customary perfume constituents.

A still further object of the present invention is the improvement in the process of supplying a pleasing odor to a product by incorporating a perfume therein, of utilizing from 0.05 to 2% by weight of the above carbonic acid esters as said perfume.

These and other objects of the invention will become more apparent as the description thereof proceeds.

DESCRIPTION OF THE INVENTION

It has been found that carbonic acid esters of the general formula $$R_1-O-\overset{O}{\overset{\|}{C}}-OR_2,$$

in which $R_1$ represents a substituted cyclohexyl radical or a cycloaliphatic radical having 8 to 12 carbon atoms, and $R_2$ represents a straight or branched chain, saturated or unsaturated aliphatic hydrocarbon radical having 1 to 5 carbon atoms, are valuable new perfumes having a very natural and complex scent.

More particularly the present invention relates to a carbonic acid ester of the formula $$R_1-O-\overset{O}{\overset{\|}{C}}-O-R_2$$

wherein $R_1$ is a member having from 8 to 12 carbon atoms selected from the group consisting of alkylcyclohexyl, alkenylcyclohexyl, alkynylcyclohexyl and cycloalkyl, and $R_2$ is a member selected from the group consisting of alkyl having from 1 to 5 carbon atoms, alkenyl having from 2 to 5 carbon atoms and alkynyl having from 2 to 5 carbon atoms. These compounds could also be called "alkyl cycloalkyl carbonates". The invention also consists of processes to produce the carbonic acid esters and to perfumery compositions.

The new compounds in accordance with the invention are produced by known processed by reacting cycloalkanols of the general formula $R_1-OH$ with chloroformic acid esters of the general formula $R_2O-COCl$, in which $R_1$ and $R_2$ have the aforementioned significance, in anhydrous, inert solvents such as hexane, benzene, toluene in the presence of a hydrochloric acid acceptor such as a equivalent of pyridine at a reaction temperature of from 0° to 5° C.

Advantageously when tertiary cycloalkanols are employed such as 1-ethynylcyclohexanol, they are first converted into the corresponding sodium alcoholate by reaction with finely distributed sodium and are then reacted with chloroformic acid esters at about room temperature in an inert solvent to give the desired carbonic acid esters.

Cyclic starting alkanols which may be mentioned are, for example, alkylcyclohexanols such as menthol, carvomenthol, trans-3,3,5-trimethylcyclohexanol, cis-3,3,5-trimethylcyclohexanol; alkenylcyclohexanols such as 3-allylcyclohexanol; alkynylcyclohexanols such as 1-ethynylcyclohexanol; cycloalkanols such as cyclooctanol, cyclononanol, cyclodecanol, cycloundecanol and cyclododecanol. In view of their availability, cyclooctanol and cyclododecanol are the most important of the last-mentioned cycloalkanols having 8 to 12 carbon atoms.

By way of example, alkyl chloroformates such as the chloroformic acid methyl esters, the chloroformic acid ethyl ester, the chloroformic acid propyl ester, the chloroformic acid i-propyl ester, the chloroformic acid n-butyl ester, the chloroformic acid i-butyl ester, the chloroformic acid tert-butyl ester, the chloroformic acid amyl ester; alkenyl chloroformates such as the chloroformic acid allyl ester; and alkynyl chloroformates such as the chloroformic acid propargyl ester, may be mentioned as reaction partners to be reacted with the cyclic alkanols, the greatest importance being attached to chloroformic acid methyl ester and chloroformic acid ethyl ester, since products having the most intensive scent are obtained with these substances.

Consequently, new perfume esters in accordance with the invention are the following carbonic acid esters methyl menthyl carbonate
methyl carvomenthyl carbonate
methyl 1-ethynylcyclohexyl carbonate
methyl trans-3,3,5-trimethylcyclohexyl carbonate
methyl cis-3,3,5-trimethylcyclohexyl carbonate methyl cyclooctyl carbonate
methyl cyclononyl carbonate
methyl cyclodecyl carbonate
methyl cycloundecyl carbonate
methyl cyclododecyl carbonate
ethyl menthyl carbonate
ethyl carvomenthyl carbonate
ethyl 1-ethynylcyclohexyl carbonate
ethyl trans-3,3,5-trimethylcyclohexyl carbonate
ethyl cis-3,3,5-trimethylcyclohexyl carbonate
ethyl cyclooctyl carbonate
ethyl cyclononyl carbonate
ethyl cyclodecyl carbonate
ethyl cycloundecyl carbonate
ethyl cyclododecyl carbonate
propyl menthyl carbonate
propyl 1-ethynylcyclohexyl carbonate
propy trans-3,3,5-trimethylcyclohexyl carbonate
propyl cyclooctyl carbonate
propyl cyclododecyl carbonate
i-propyl 1-ethynylcyclohexyl carbonate
i-propyl cis-3,3,5-trimethylcyclohexyl carbonate
i-propyl cyclooctyl carbonate
i-propyl cyclodecyl carbonate
i-propyl cycloundecyl carbonate
i-propyl cyclododecyl carbonate
tert-butyl 1-ethynylcyclohexyl carbonate
tert-butyl cis-3,3,5-trimethylcyclohexyl carbonate
tert-butyl cyclooctyl carbonate
tert-butyl cyclodecyl carbonate
tert-butyl cycloundecyl carbonate
tert-butyl cyclododecyl carbonate
amyl trans-3,3,5-trimethylcyclohexyl carbonate
amyl cyclooctyl carbonate
amyl cyclononyl carbonate
amyl cyclododecyl carbonate
allyl 1-ethynylcyclohexyl carbonate
allyl cis-3,3,5-trimethylcyclohexyl carbonate
allyl cyclooctyl carbonate
allyl cyclododecyl carbonate
propargyl trans-3,3,5-trimethylcyclohexyl carbonate
propargyl cyclooctyl carbonate
propargyl cyclododecyl carbonate The most important of the aforementioned compounds suitable as new perfumes are methyl 1-ethynylcyclohexyl carbonate, methyl cis-3,3,5-trimethylcyclohexyl carbonate, methyl trans-3,3,5-trimethylcyclohexyl carbonate, methyl cyclooctyl carbonate, ethyl trans-3,3,5-trimethylcyclohexyl carbonate and ethyl cyclooctyl carbonate.

The new perfume esters in accordance with the invention are distinguished by particularly intensive and lasting flowery, herbal, fruity and fresh scents of high quality and fullness. A further advantage of the new perfume esters is that they can be very satisfactorily combined to form novel nuances of fragrance and that they have a particularly high degree of persistence.

The new perfume esters in accordance with the invention may be mixed with other perfumes in a wide range of quantity ratios to form new perfumery compositions. However, in general, the proportion of the new perfume esters in the perfumery compositions will be from 1 to 50% by weight relative to the total composition. The remainder of the composition is conventional perfume constituents. Such compositions can act directly as perfumes or, alternatively, to perfume cosmetics such as creams, lotions, toilet waters, aerosols, toilet soaps etc. Alternatively, however, they may be used to improve the odor of technical products such as washing and cleaning agents, disinfectants, agents for treating textiles etc., as is also possible in the case of the new compounds themselves.

The present invention will now be further described by means of the following Examples which are not to be limitative in any manner.

EXAMPLES

The production of the new perfumes will be described in the first instance.

EXAMPLE 1

Methyl cyclooctyl carbonate 18.9 gm of methyl chloroformate were added drop-by-drop under agitation to a solution of 25.6 gm of cyclooctanol and 15.8 gm of absolute pyridine in 150 ml of dry benzene under external cooling at 0° to 5° C. After the methyl chloroformate had been added, agitation was continued for 12 hours at room temperature. Then, the benzene phase was drawn off from the precipitated pyridine hydrochloride, and washed with diluted hydrochloric acid, sodium hydroxide solution and water, and dried. After the solvent had been distilled off, the raw ester was distilled in vacuo by means of a Vigreux column. A colorless liquid was obtained which had a herbal, very natural and complex fragrance which is distinguished by a strong and long-clinging flowery jasmine scent.

Characteristic values:

Boiling point — 47° C at 0.01 mm Hg
Refractive index — $n_D^{20}$ = 1.4580
IR (film) — 1735, 1445, 1275, 945, 800/cm
NMR ($CCl_4$) — δ = 1.60 (m), 14 H; 3.7 (s), 3 H ($-OCH_3$); 4.75 (m), 1 H ppm

EXAMPLE 2

Ethyl cyclooctyl carbonate

The product was obtained similarly as in Example 1 by reacting cyclooctanol with ethyl chloroformate and a colorless liquid was obtained.

Odor: — flowery, sweet, fruity, very natural and complex, syringa fragrance
Boiling point — 55° C at 3.0 mm Hg
Refractive index $n_D^{20}$ = 1.4572
IR (film) — 1730, 1450, 1265, 953, 790/cm
NMR ($CCl_4$) — δ = 1.27 (t), J = 7 Hz, 3 H ($C-CH_3$); 1.57 (m), 14 H; 4.08 (q) J = 7 Hz, 2 H ($O-CH_2-C$); 4.75 (m), 1 H (CH—O) ppm.

EXAMPLE 3

Methyl trans-3,3,5-trimethylcyclohexyl carbonate

This substance was produced, analogously to Example 1, from trans-3,3,5-trimethylcyclohexanol and methyl chlorofomate.

Odor: — earthy, fruity, very natural smell, fragrance of forest soil or humus.
Boiling point — 88° C at 3.2 Hg; colorless liquid
Refractive index $n_D^{20}$ = 1.4428
IR (film) — 1750, 1445, 1275, 1240, 1180, 930/cm
NMR ($CCl_4$) — δ = 3.65 (s), 3 H ($OCH_3$); 4.87 (m), 1 H (CH—O) ppm

EXAMPLE 4

Ethyl trans-3,3,5-trimethylcyclohexyl carbonate

The substance was produced from trans-3,3,5-trimethylcyclohexanol and ethyl chloroformate in accordance with the procedure given in Example 1.

Odor: — fruity, camphoric, similar to piconia, suitable for cedar fragrances
Boiling point — 56° C at 0.01 Hg; colorless liquid
Refractive index — $n_D^{20} = 1.4412$
IR (film) — 1740, 1375, 1270, 1240, 1180, 1010/cm
NMR ($CCl_4$) — $\delta = 1.32$ (t), J = 7 Hz, 3 H; 4.17 (q), J = 7 Hz, 2 H; 4.95 (m), 1 H ppm.

EXAMPLE 5

Methyl cis-3,3,5-trimethylcyclohexyl carbonate

The substance was produced, anaolgously to Example 1, from cis-3,3,5-trimethylcyclohexanol and methyl chloroformate.

Odor — very natural, fresh, metallic, suitable for artifical neroli petitgrain palmarosa oil
Boiling point — 60° C at 0.1 mm Hg; colorless liquid
Refractive index — $n_D^{20} = 1.4401$
IR (film) — 1750, 1445, 1270, 1240, 960/cm
NMR ($CCl_4$) — $\delta = 3.6$ (s), 3 H; 4.66 (m), $J_{ae} = 4.5$ Hz, $J_{aa} = 11.5$ Hz, 1 H ppm

EXAMPLE 6

Methyl 1-ethynylcyclohexyl carbonate

A solution of 36.0 gm of 1-ethynylcyclohexanol in 50 ml of benzene was slowly added drop-by-drop to an agitated suspension, cooled to 0° to 5° C, of 5.5 gm of finely distributed sodium in 50 ml of absolute toluene and 250 ml of benzene, and was agitated at room temperature until reaction had been completed. 26.0 gm of methyl chloroformate were added under cooling to the sodium salt which has been formed. The mixture was allowed to react for 12 hours at room temperature and was washed several times with water and dried. After distilling off the solvent, the raw ester was fractionated by means of a 20 cm Vigreux column. The methyl 1-ethynylcyclohexyl carbonate thus obtained constitutes a coloroless liquid having a fruity, herbal, complex odor and a distinctive fragrance of dill, and has the following characteristic values;

Boiling point — 47° C at 3.5 mm Hg
Refractive index — $n_D^{20} = 1.4630$
IR (film) — 3280, 2940, 2110, 1755, 1440, 1280, 1245, 1020/cm
NMR ($CCl_4$) — $\delta = 1.1 - 2.4$ (m), 10 H; 2.55 (s) 1 H ($C \equiv CH$); 3.7 (s), 3 H ($OCH_3$) ppm All the compounds given in the above Examples have natural flowery, herbal, fruity, fresh fragrances with excellent clinging properties or persistency which render them suitable for producing a wide variety of perfume compositions. Such compositions can be used to perfume a wide variety of products such as cosmetics, washing agents, soaps as well as technical products in concentrations of approximately 0.05 to 2% by weight. Examples of perfumery compositions having a content of the new perfume esters in accordance with the invention are given hereinafter.

EXAMPLE 7

"Jasmine" perfume composition

Methyl cyclooctyl carbonate — 230 parts by weight
Benzyl acetate — 350 parts by weight
Linalool — 60 parts by weight
Linalyl acetate — 60 parts by weight
Hydroxycitronellal — 60 parts by weight
Ylang oil I — 40 parts by weight
Aurantesin B, H&R — 25 parts by weight
Hedion, Firmenich — 25 parts by weight
Lilial L. G. — 20 parts by weight
Benzyl salicylate — 35 parts by weight
Geranyl acetate — 25 parts by weight
Aldehyde C 14 so-called 10% — 15 parts by weight
Isoraldein 70 L. G. — 15 parts by weight
Paracresylphenyl acetate 10% — 15 parts by weight
Phenylethyl acetate — 20 parts by weight
Indoflor H&R — 5 parts by weight

EXAMPLE 8

Wood base perfume composition

Ethyl trans-3,3,5-trimethylcyclohexyl carbonate — 500 parts by weight
Oryclon — 100 parts by weight
Vetiveryl acetate — 1C0 parts by weight
Sandalwood oil — 100 parts by weight
Isoraldein 70 — 50 parts by weight
Guaiyl acetate — 50 parts by weight
Cumarine — 50 parts by weight
Phenylethyl alcohol — 50 parts by weight In the preceding Examples 7 and 8 a number of ingredients were indicated by tradename. These ingredients are as follows:

Aurantesin B, H & R - A Schiff's base from the methyl ester of anthranilic acid + hydroxycitronellal
Hedion, Firmenich - methyl dihydrojasmonate
Lilial L. G. - 4-tert.-butyl-$\alpha$-methyl-hydrozimtaldehyde
Aldehyde C 14 - $\gamma$-undecalactone
Isoraldein 70 L. G. - a mixture of $\alpha$, $\beta$- and $\gamma$-methylionone
Indoflor, H and R - Indeno-dioxan having the formula

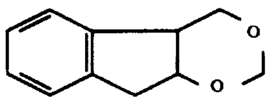

Orylon - cis-/trans-p-tert.-butyl-cyclohexyl acetate

EXAMPLE 9

Soap perfume composition

Citrenes — 450 parts by weight
Ethyl cyclooctyl carbonate — 325 parts by weight
Methyl anthralinate — 100 parts by weight
Indole — 5 parts by weight
Bergamot oil — 70 parts by weight
Tolu balsam — 50 parts by weight This soap perfume composition is added to a toilet soap in amounts of from 0.5 to 1% by weight.

The preceeding specific embodiments are illustrative of the practice of the invention. It is to be understood however, that other expedients known to those skilled in the art or disclosed herein may be employed without departing from the spirit of the invention or the scope of the appended claims.

We claim:

1. A carbonic acid ester of the formula

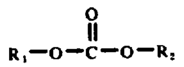

wherein $R_1$ is cycloalkyl having from 8 to 12 carbon atoms, and $R_2$ is a member selected from the group consisting of alkyl having from 1 to 5 carbon atoms, alkenyl having from 2 to 5 carbon atoms and alkynyl having from 2 to 5 carbon atoms.

2. The carbonic acid ester of claim 1 wherein $R_1$ is a member selected from the group consisting of cyclooctyl and cyclododecyl.

3. The carbonic acid ester of claim 1 wherein $R_2$ is a member selected from the group consisting of methyl and ethyl.

4. The cabonic acid ester of claim 1 wherein $R_1$ is methyl and $R_2$ is cyclooctyl.

5. The carbonic acid ester of claim 1 wherein $R_1$ is ethyl and $R_2$ is cyclooctyl.

* * * * *